United States Patent
Razavi

[11] Patent Number: 5,676,685
[45] Date of Patent: Oct. 14, 1997

[54] TEMPORARY STENT

[76] Inventor: Ali Razavi, 9100 Old Indian Hill Rd., Cincinnati, Ohio 45243

[21] Appl. No.: 494,555

[22] Filed: Jun. 22, 1995

[51] Int. Cl.$^6$ .................................................. A61M 29/00
[52] U.S. Cl. ........................... 606/194; 606/198; 606/192
[58] Field of Search ........................ 623/1, 12; 606/191, 606/198, 194, 195, 200

[56] References Cited

U.S. PATENT DOCUMENTS

| | | |
|---|---|---|
| 4,503,569 | 3/1985 | Dotter . |
| 4,553,545 | 11/1985 | Maass et al. . |
| 4,649,922 | 3/1987 | Wiktor . |
| 4,690,684 | 9/1987 | McGreevy et al. . |
| 4,731,073 | 3/1988 | Robinson ................................. 623/1 |
| 4,733,665 | 3/1988 | Palmaz . |
| 4,739,762 | 4/1988 | Palmaz . |
| 4,743,252 | 5/1988 | Martin, Jr. et al. . |
| 4,771,773 | 9/1988 | Kropf . |
| 4,773,432 | 9/1988 | Rydell . |
| 4,776,337 | 10/1988 | Palmaz . |
| 4,787,900 | 11/1988 | Yannas . |
| 4,850,999 | 7/1989 | Planck . |
| 4,856,516 | 8/1989 | Hillstead . |
| 4,871,365 | 10/1989 | Dumican . |
| 4,886,062 | 12/1989 | Wiktor . |
| 4,902,289 | 2/1990 | Yannas . |
| 4,997,440 | 3/1991 | Dumican ................................. 623/1 |
| 5,019,090 | 5/1991 | Pinchuk . |
| 5,078,736 | 1/1992 | Behl . |
| 5,098,440 | 3/1992 | Hillstead . |
| 5,102,417 | 4/1992 | Palmaz . |
| 5,116,360 | 5/1992 | Pinchuk et al. . |
| 5,116,365 | 5/1992 | Hillstead . |
| 5,123,917 | 6/1992 | Lee ........................................ 623/1 |
| 5,133,732 | 7/1992 | Wiktor . |
| 5,222,969 | 6/1993 | Gillis . |
| 5,282,823 | 2/1994 | Schwartz et al. .................... 606/198 |
| 5,292,321 | 3/1994 | Lee ..................................... 606/28 |
| 5,370,691 | 12/1994 | Samson .............................. 623/12 |
| 5,443,495 | 8/1995 | Buscemi et al. ..................... 623/1 |
| 5,500,013 | 3/1996 | Buscemi et al. ..................... 623/1 |

*Primary Examiner*—Michael Buiz
*Assistant Examiner*—Patrick W. Rasche
*Attorney, Agent, or Firm*—Vidas, Arrett & Steinkraus, P.A.

[57] ABSTRACT

This invention concerns an improved removable stent for temporary placement within a body. A stent according to the present invention utilizes a removable coil or the like of reinforcing filament such as metal or plastic wire enclosed at least partially within a shell or within a covering of biodegradable/bioabsorbable material which is allowed to remain within the body after removal of the reinforcing filament.

15 Claims, 5 Drawing Sheets

5,676,685

TEMPORARY STENT

BACKGROUND OF THE INVENTION

The present invention relates to the type of endoprosthesis devices commonly known as stents. More particularly, it relates to stents of the type intended for temporary implantation within a body vessel, duct, urinary tract or the like.

Stents are usually placed or implanted within a blood vessel for example for treating stenoses, strictures or aneurysms. The purpose is to reinforce collapsing, partially occluded, weakened or abnormally dilated sections of a vessel or duct. For example, one common procedure in partially occluded blood vessels is to first open the region in the vessel with a balloon catheter and then place a stent in a position that bridges that region of the vessel.

One technique for implanting a stent uses a balloon catheter to position the stent within a vessel. Once the stent is properly positioned, the balloon is withdrawn, leaving the stent in place. In some cases, the balloon may be inflated during placement to press the stent against the inner wall of the vessel before being withdrawn.

SUMMARY OF THE INVENTION

The improved temporary stent of the invention is comprised of two main elements, one being a two-layer biodegradable/bioabsorbable (bio-materials herein generally) element and the other being a reinforcing wire, core body or a like element which may be removed at some time following implantation of the stent, leaving the "bio" element to gradually disappear on its own over time.

Typically, the reinforcing element core body will comprise a core of coil spring shape to provide radial support from within the stent while allowing for removal of the core by merely pulling it out through a guiding catheter or the like.

DETAILED DESCRIPTION OF THE INVENTION

Figure 1:
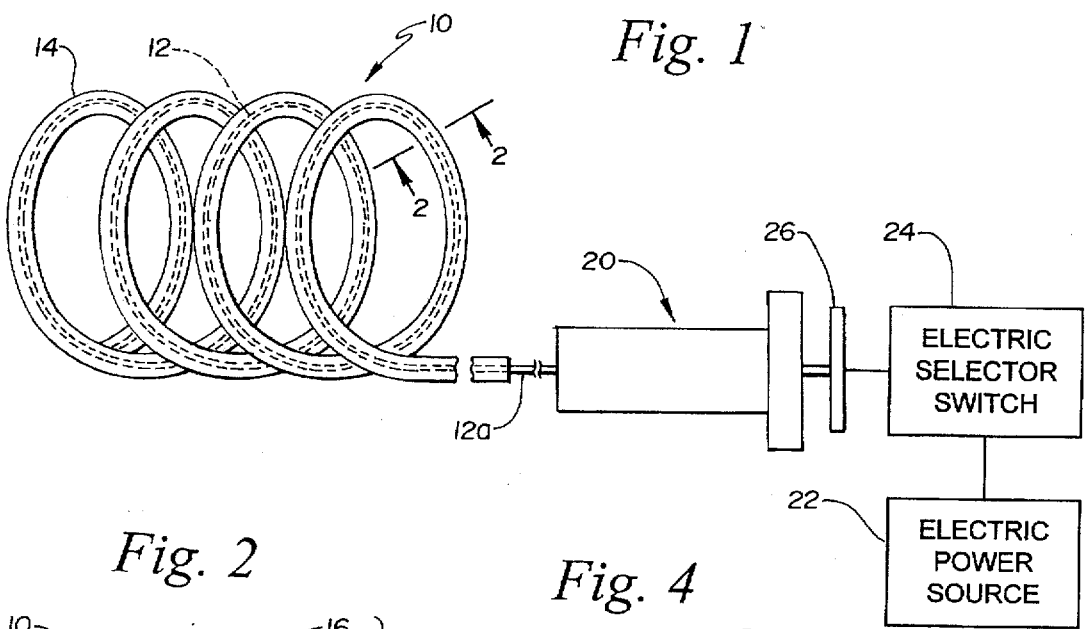
FIG. 1 is a partly schematic illustration of a first embodiment of a temporary stent according to the invention after emplacement, the stent size being somewhat exaggerated for descriptive purposes.
Figure 2:
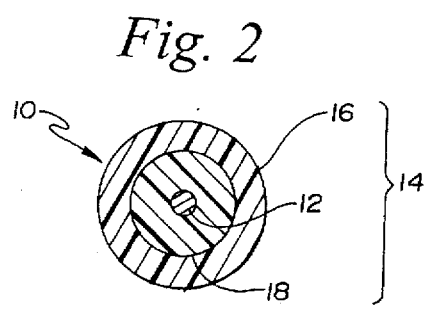
FIG. 2 is a cross-section view taken along line 2—2 of FIG. 1.
Figure 3A:
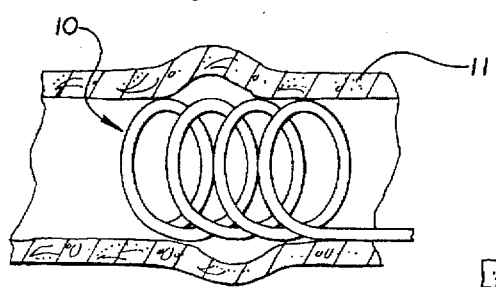
FIG. 3a is a simplified sectional view showing the coil of FIG. 1 in relation to an artery which contains an aneurysm.
Figure 3:
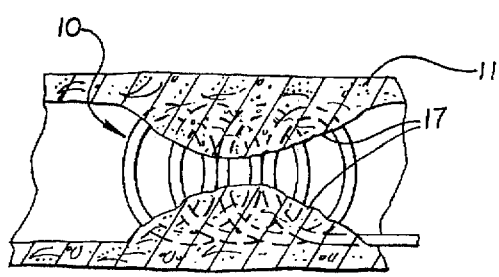
FIG. 3 is a simplified sectional view showing the coil of FIG. 1 in relation to an artery.

Referring to FIGS. 1, 2 and 3 and the embodiment shown therein, assume that stent 10 has been initially placed within a vessel 11 (see FIG. 3) or the like. Stent 10 is comprised of a wire coil 12 enclosed within a sheath or coating indicated at 14 of biodegradable/bioabsorbable material. Coil 12 may be tightly wound or coiled around a catheter, assuming a small diameter for placement. Upon release the spring-like material causes it to self-expand. On the other hand, it may be deformable and expandable mechanically as by a balloon inside the stent. Both approaches are known in the art.

Coating 14 is preferably made up of two layers 16 and 18, respectively as best seen in FIG. 2. Although both layers 16 and 18 are a "bio" material, layer 18 is also of a material selected to soften or even liquify at some predetermined safe elevated temperature that is above body temperature but below about 60° C. so as to be safe. Thus, upon being exposed to such a temperature, layer 18 softens to release core wire 12 so that it can be pulled through guiding catheter 20 and removed from the emplacement, leaving only the bio material 14 in place. Removal of core wire 12 will of course be accomplished at such time as the stent has served its temporary purpose.

Core wire 12 may for example be metal such as stainless steel or gold or other relatively pliable non-toxic metals and alloys that do not degrade during the time of implantation or are not subject to severe degradation (corrosion) under the influence of an electric current. Such metals include but are not limited to platinum, platinum-iridium alloys, copper alloys, with tin or titanium, nickel-chrome-cobalt alloys, and nickel-titanium alloys. Such metal cores may for example be between about 0.005 to 0.008 inches in diameter. Of course, the diameter could vary depending on lumen size and degree of support needed. The core need not be metal and may for example be of a polymeric material such as an elastomer, a polyester or the like. In general, any material acceptable to the body and capable of being formed into an elongate filament-like configuration, which can be used to transfer heat and which can be configured for temporary reinforcement purposes and still pulled loose for removal will be satisfactory for the purposes of this invention. The filament may be metal, inorganic fibers or organic polymers.

Polymeric materials and composites that can be formed into elongate filaments and which can be configured for providing reinforcement include polyethylene-terephthalate (PET), polyimides, high durometer polyurethanes, polyacrylontride, high strength polyethylene and polyamides. High strength fibers, such as boron, aluminum oxide, aluminum-boria-silica, silicon nitride and graphite-epoxide may be used. Very thin (25–50 micrometer diameter) strands of flexible, high strength material, such as liquid crystalline materials when combined with materials that soften to provide a mechanism such that the softer material maybe removed without breaking cracking, may be used. Thus, conductive high strength graphite fiber may be combined with a low durometer polyurethane to form the core 12.

Materials that are not normally conductive may be made so as by applying thin flexible coatings of gold by ion vapor depositions or the like or by incorporating metallic particles into extrusions of such materials. Core 12 can be made of a composite so constructed that a normally non-conductive supportive portion may include a central conducting metallic wire or soft flexible metallic wires or graphite fibers, which are conductive, woven into strands with a supporting non-conductive element.

As to the "bio" material 14, layer 16 may be any biodegradable or bioabsorbable material such as for example: polycaprolactone, polylactic acid, polylactic acid-glycolic acid, polyurethane or other "bio" materials either alone or in combination with other materials which might be used as the vessel wall contacting element of the stent. Preferably, the material of layer 16 will not be substantially affected by the heat applied to the stent. Such materials include DOW2363 polyurethane (DOW-Midland, Mich.), MDX 4210 silicone rubber and polyvalerolactone.

This layer may also include quantities of such materials as: anti-thrombotic, anti-platelet, vasodialators, anti-proliferative agents and more specifically, Heparin, Himdin, Himlog (an anti-thrombotic produced by Biogen, Inc. of Cambridge, Mass. 02142), Etritinate (an anti-proliferative, generic for Tegison and the like supplied by Rache Dermatologist of Nutly, N.J. 07110), Freskolin (an antithrombotic and vasodilator) and the like.

Layer 18, as already indicated, is also a "bio" material but it has the property of softening or liquefying at a safe elevated temperature above body temperature, i.e., between about 45°–60° C. Polyurethane is an example of such a material. Polyurethanes that have about 40 mole percent of soft segment comprised of polyethers can be formulated to soften in the desired temperature ranges. Polycaprolactone is another example. Also, polyesters such as poly-1-lactides poly-1-glycolides and polybutene terephthalates may be used. Copolymers such as expoxides and polyamides may also be formulated with softening segments of silicone rubber. Nylon 6/6 with about 10 to 30 volume percent of polymethylsiloxane as a copolymer may be used. Polyaliphatics such as polyethylene may be combined with plasticizers such as dibutyl adipate or polyester adipate or glycerol derivatives may be tailored to soften in the safe temperature range. Polymeric materials such as low molecular weight polyethylene having a MW between about 1000 to 50,000 may be used. Copolymers of polyethylene with polyamides may be formulated to soften or become fluid. Polycaprolactone may be used as layer 18. Polyethylene oxide (PEO) of molecular weight 1000 to about 10,000 will liquify in the desired temperature range as well composites of PE and PEO in that molecular weight range. These materials can be heated by convection.

The thickness of these layers 16 and 18 may vary depending on use and material but will generally be between 10 to 100 micrometers in thickness and preferably about 20–40 micrometers. The criteria for thickness rests in the ability of the layer 16 to support the vessel when layer 18 is softened or the like.

As shown in FIG. 1, the temporary stent 10 upon being implanted in a body may continue to be attached to a long lead portion means 12a extending through guiding catheter 20 until time for removal. On the other hand, it may be detached and reattached at time of removal by means of a suitable connector (not shown) When removal is desired the power source 22, properly connected for operation to lead 12a through elements 24 and 26, is activated and core wire 12 heats up to cause softening of layer 18 upon which the proximal end of lead 12a may be pulled to remove core wire 12 from the stent.

Layer 18 is preferably heated by electrical heating, although laser radio frequency (RF) or any other energy source may be used. In the case of FIG. 1, electrical resistance heating is used by means of a power source which may be connected to electrically conductive core wire 12 by means of an electric selector switch 24 and a connector plug 26. Layer 18 is positioned functionally in the stent so as to be disposed between layer 16 and core 12. When it "releases" upon softening, due to heating of core 12, core 12 may be readily pulled out with minimal disturbance of layer 16, leaving layer 16 in place. Some of layer 18 biomaterial may be removed with core 12 and some may remain in place. More specifically, when layer 18 releases upon softening, core 12 is readily pulled out. Layer 18 remains in place, or if it liquifies, portions of layer 18 may remain attached to core 12 and resolidify upon reducing energy input. If layer 18 is essentially water insoluble, such as low molecular weight PE, it will not dissolve into the blood should that occur. If the layer is not melted but only softened, then core 12 will slip through layer 18, leaving it totally in place.

Generally, the loop or coil structure is preferred for placement due to the convenience of its easy removal on being pulled out. However, other configurations, particularly other radial configurations which may readily be pulled loose, will become apparent to those familiar with this art. Also, although the core is shown as a typical round in cross-section wire, there is no reason that other cross-section configurations such as flat and the like could not be used, the former however is presently preferred.

Thus, it can be seen that in one embodiment of the invention, a coated coiled stent is placed and remains in physical contact with a transcutaneous insertion point by means of a wire core or the like. Upon application of heating energy to the stent through the core, the coating or a portion thereof is allowed to remain in place while the core is removed. The core not only functions as a reinforcement element but as an energy conduit. The outer layer 16 or coating is preferably not to be significantly affected by the heat whereas the middle layer 18 is softened or melted, enabling removal of the core portion 12.

Figure 8:
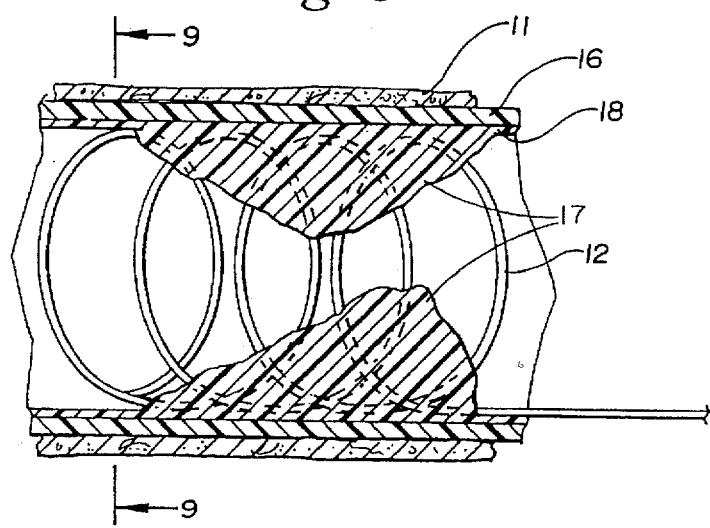
FIG. 8 is another embodiment of the invention in which the reinforcing coil element is placed within a tubular shell of the bio element.
Figure 10:
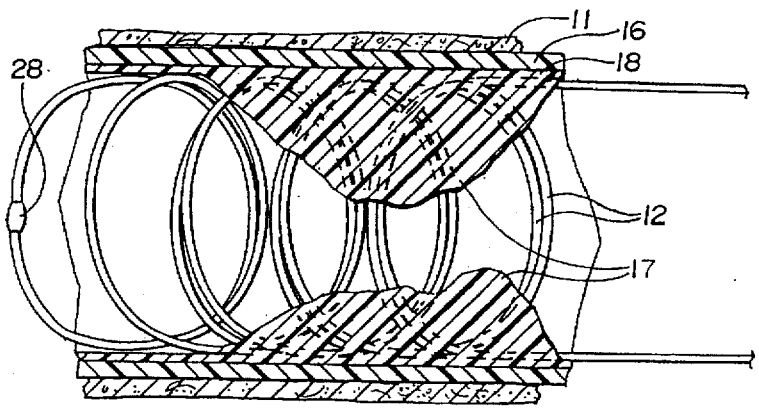
FIG. 10 is yet another embodiment of the invention including aspects of FIG. 3 and FIG. 7.

As shown in FIGS. 3, 8 and 10, during typical procedures the damaged vessel or duct wall is collapsed in the lumen 17. The exception would be in the case of aneurysm repair, in which case there might be some outward bulging of the vessel wall as shown in FIG. 3a.

Figure 4:
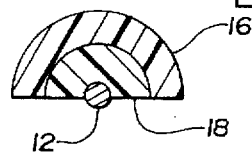
FIG. 4 is a cross-section of an alternate embodiment of the stent of FIG. 1.

Referring now to FIG. 4, another version of stent construction is shown in which core wire 12 is only partially enclosed or encapsulated by element 14 (layers 16–18). In effect, in this embodiment core 12 lies in a groove in layer 18. When wound into a coil or similar configuration, this structure is positioned so as to present layer 16 to the vessel wall with the core 12 being disposed toward the interior. It may be removed in the same fashion as the embodiment of FIG. 1. It can be seen that the concept is broadly to provide a contacting layer 16, an intermediate layer 18 and an inner core body 12.

In the event electrically heating or the like is not desired, fiber optic wire may be used in place of core wire 12. It will heat upon being exposed at its proximal end 12a to laser energy. Again, the broad concept is to provide means for providing an appropriate stimulus to layer 18 so as to change its condition from a solid condition to a "release" condition such as a softened condition.

Quartz fiber or high quartz glass of 500 microns in diameter or thereabout may be used as optical fiber and to form supporting reinforcement. However, the softening point is well above the "safe" temperature range of interest. If such fibers were formed into a coil, they would be difficult to withdraw. If the coil so formed were of smaller diameter than the expanded diameter and, therefore dependent on layer 18 and/or 16 to hold the device in the expanded position, then the function of support (reinforcement) would reside in element 14 (layer 16 and/or 18). Multiple thin fibers may be constructed to be sufficiently flexible to be removed but not also for support. Therefore, in most cases if radiation is to be used as the source of energy, very thin flexible fibers must be combined with other structural components.

Figure 5:
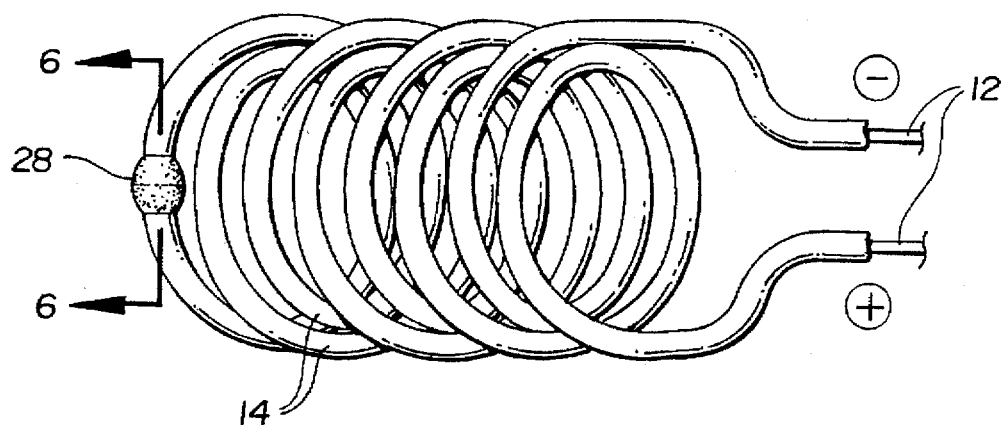
FIG. 5 is a view similar to that of FIG. 1 showing another embodiment of the invention, including a double coil or helix reinforcement element which may be fused for removal.
Figure 6:
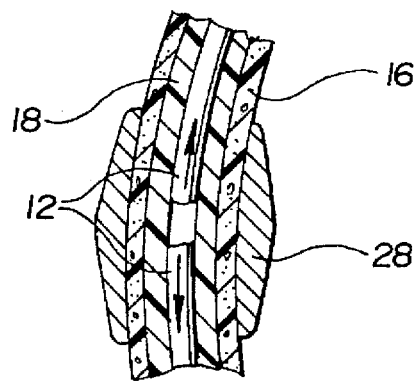
FIG. 6 is a sectional view taken along line 6—6 of FIG. 5 showing the core wire separating and retracting after being heated by electrical energy.

Referring now to FIG. 5, a double core wire version of the invention is shown. In other respects it is similar to that of FIG. 1 in that core wires 12 are coated with the two-layer "bio" material as before. However, in this embodiment, the core wires 12 are used in a helix-like double loop configuration as shown in FIG. 5. Optionally, if an electrical resistance heating approach is to be used for heating the inner layer 18, the core 12 may include a section which is linked together at 28 by a fusible material which melts as shown in FIG. 6 at the heating temperature generated in the cores by the source of energy such as shown in FIG. 1. Of course the cores need not be fused together or even joined at their distal ends in any way. In such event, another arrangement and means for heating may be utilized. Also, the variation of FIG. 4 may be used in the embodiment of FIG. 5.

Figure 7:
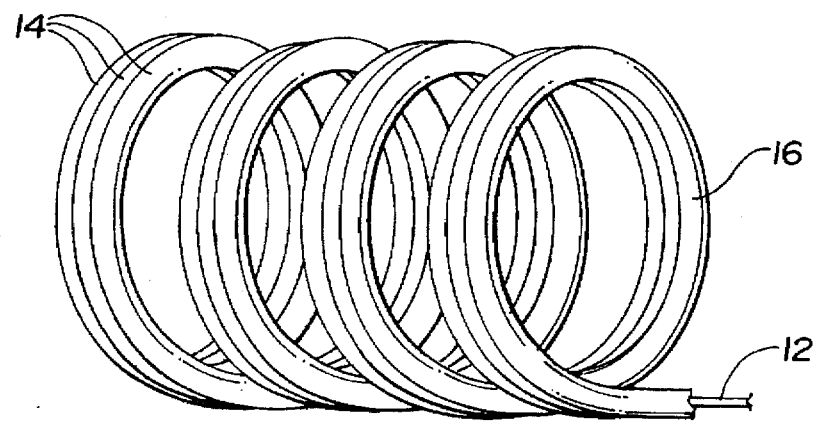
FIG. 7 is a showing of a triple reinforcement element which may be used in the invention.

FIG. 7 is included to illustrate that more than two cores may be used. In this Figure three coated cores 14 are illustrated in this version.

Figure 9:
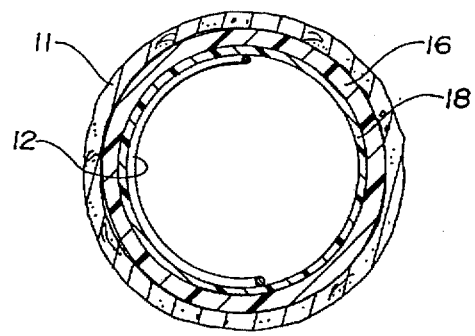
FIG. 9 is a cross-section taken along line 9—9 of FIG. 8.

Turning now to the embodiment shown in FIG. 8 and FIG. 9, a slightly different approach is used. In this version, the "bio" material may be a single layer 16 of material which is selected to have mechanical support properties so as to form a tube. Layer 18 is not required in this version but may be optionally included as shown. A single reinforcing coil 12 is carried within the tubular configuration of the stent and may be removed by simply pulling it out when desired. Typically, temporary stents are in place for 12–68 hours or so. It may be that tubular material 16 be formed with openings (not shown) therein for circulation. These may be formed by mechanical or chemical means such as drilling, laser penetration, etching, dissolution or soluble component, etc.

FIG. 10 shows a version similar to that of FIGS. 8 and 9 and similar to FIG. 5 in that two cores 12 are used in the tube 16. As in FIG. 5, cores 12 may be fused at 28 if desired and layer 18 may be optionally included.

Figure 11:
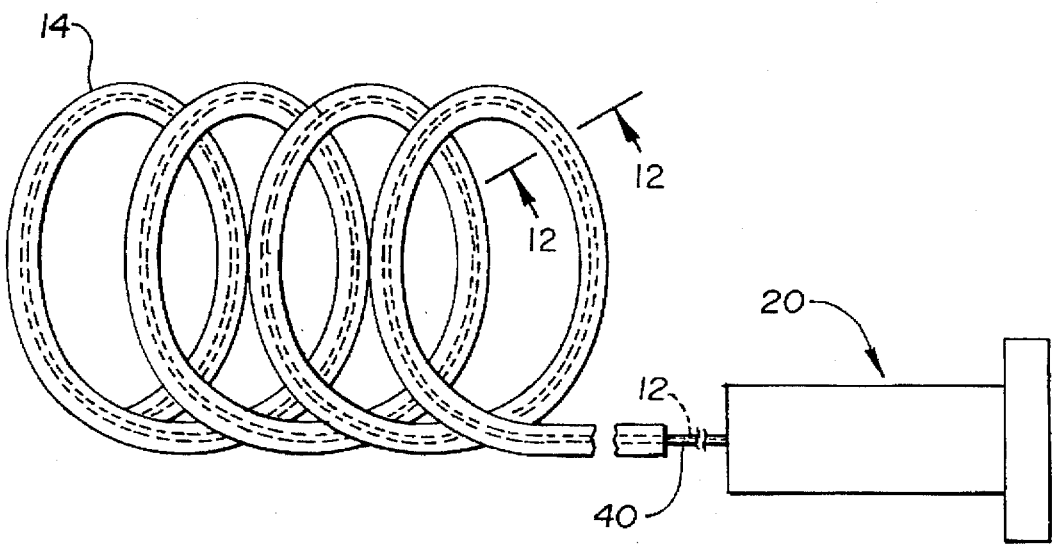
FIG. 11 is still another embodiment of the invention incorporating a balloon around the reinforcement element for facilitating removal.
Figure 12:
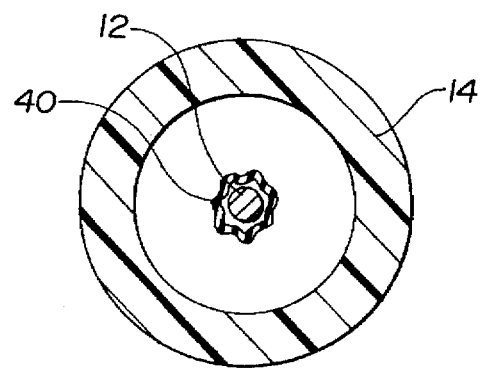
FIG. 12 is a cross-section taken along line 12—12 of FIG. 11.

Referring to FIGS. 11 and 12, yet another approach is shown that is similar to FIGS. 1–2 in that core wire 12 is sheathed in bio material element 14. However, an elongate balloon 40 such as that used in angioplasty PTCA applications is also included. Balloon 40 is arranged to enclose core 12 over its length inside the stent proper as shown. During implant it is inflated. When removal is desired, it is deflated and removed along with core 12 by pulling it out through the guiding catheter.

Figure 13:
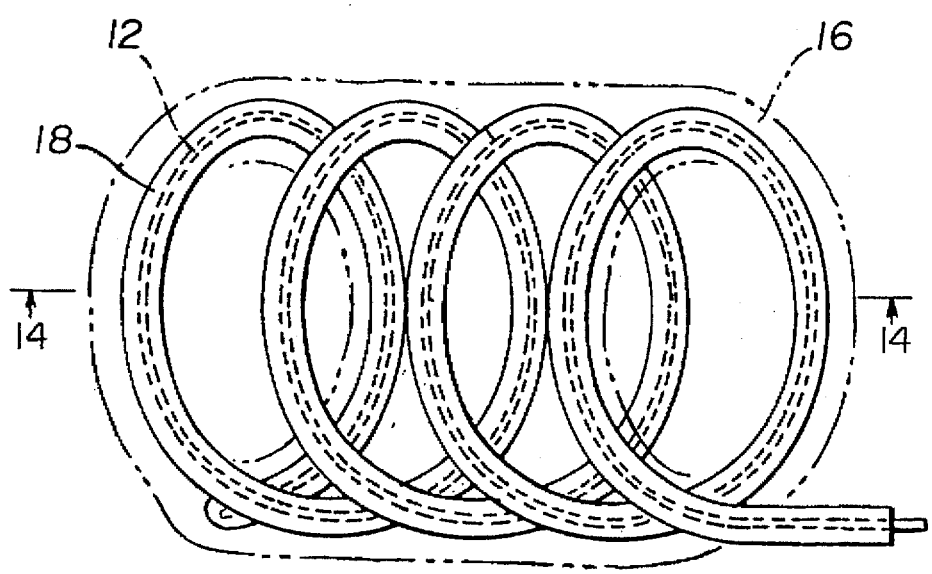
FIG. 13 is another embodiment of the invention in which the reinforcing coil element and its bio layer are contained within a cylindrical tube of biomaterial.
Figure 14:
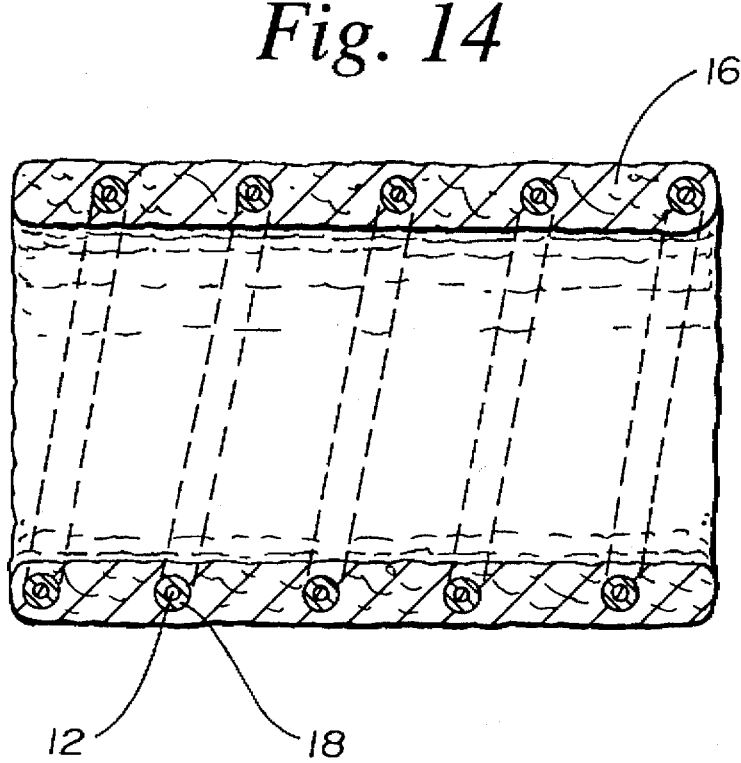
FIG. 14 is a cross-section taken along line 14—14 of FIG. 13.

FIGS. 13 and 14 demonstrate another embodiment of the invention which is similar to FIG. 10, except that in this case the core wire 12 and "bio" layer 18 are engulfed in a cylindrical tube or sleeve composed of biomaterial 16. FIG. 14 illustrates a cross-sectional view of FIG. 13 showing the core wire 12 and its layer covering 18 embedded in biomaterial 16.

Catheter connection to the balloon for inflation/deflation are as typically used in PTCA and need not be described in detail.

The biodegradable material may also be used as an outer layer on a Nitinol™ stent which could be removed after its purpose is accomplished leaving the biomaterial against the vessel wall or the kind, hence preventing disruption of the vessel walls healing process.

The stent may also be covered by a protective sleeve (not shown) which would be removed after crossing the lesion and correct positioning is achieved just before the balloon inflation.

While this invention may be embodied in many different forms, there are described in detail herein specific preferred embodiments of the invention. This description is an exemplification of the principles of the invention and is not intended to limit the invention to the particular embodiments illustrated.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A removable stent comprising in combination:
   a first body of biomaterial in predetermined configuration for lining a body passageway and having proximal and distal end portions and an exterior surface constructed and arranged for contacting the interior wall of the passageway when inserted therein;
   at least one elongate removable core body of similar predetermined configuration to that of the first body, at least partially being in the form of a coil, and with proximal and distal ends, the core body being conductive and positioned with respect to the first body so as to reinforce it;
   means attached to the proximal end of the core body for removal of the core body from the first body; and
   an intermediate second body of biomaterial positioned between the first body and the core body, the intermediate second body having the property of changing from a solid condition to a release condition upon application of a stimulus thereto, whereby the core body can be removed while the stem is within the body passageway.

2. The stent of claim 1 in the configuration of a coil, the biomaterials enclosing the core body over its length.

3. The stent of claim 1 in the configuration of a coil, the biomaterials only partially enclosing the core body over its length.

4. The stent of claim 1 in the configuration of a coil.

5. The stent of claim 4 in which the biomaterials at least partially enclose the core body over its length.

6. The stent of claim 4 including at the distal end a fusible link in the core body, the core body being conductive so as to soften the link when desired.

7. The stent of claim 1 in which a balloon including means for inflating/deflating same is included which extends over the length of the core body enclosing same.

8. The stent of claim 1 wherein the core body and the intermediate second body are engulfed in the first body of biomaterial.

9. The stent of claim 8 wherein the first body of material is a cylindrical sleeve.

10. The stent of claim 1 wherein the first body comprises a plurality of layers of biomaterial situated between the body of the stent and the interior wall of the passageway when inserted therein, the layers aiding in the facilitation of the stent's removal from the passageway while preventing disruption of the healing process of the walls of the passageway and supplying additional support.

11. A removable stent comprising in combination:

a first body of biomaterial in the form of a tube for lining a body passageway and having proximal and distal end portions and an exterior surface constructed and arranged for contacting the interior wall of the passageway when inserted therein;

at least one elongate removable core body in the form of a coil carried within the tube having proximal and distal ends the core body being positioned with respect to the first body so as to reinforce it;

means attached to the proximal end of the core body for the removal of the core body from the first body, which may be achieved by pulling on the means; and an intermediate second body of biomaterial, the second body being included as a lining of the tube and positioned between the first body and the core body, the intermediate second body having the property of changing from a solid condition to a release condition upon application of a stimulus thereto, whereby the core body can be removed while the stent is within the body passageway.

12. The stent of claim 11 in which the core body comprises a double coil.

13. A removable stent comprising in combination:

a first body of biomaterial in the form of a cylindrical sleeve for lining a body passageway and having proximal and distal end portions and an exterior surface constructed and arranged for contacting the interior wall of the passageway when inserted therein;

at least one elongate removable core body of similar predetermined configuration and with proximal and distal ends, the core body being positioned with respect to the first body so as to reinforce it;

means attached to the proximal end of the core body for the removal of the core body from the first body, which may be achieved by pulling on the means; and an intermediate second body of biomaterial positioned between the first body and the core body, the intermediate second body having the property of changing from a solid condition to a release condition upon application of a stimulus thereto, whereby the core body can be removed while the stent is within the body passageway, wherein the core body and the intermediate second body are engulfed in the first body of biomaterial and wherein the core body and the intermediate body are in the configuration of a coil.

14. The stent of claim 13 wherein the biomaterials at least partially enclose the core body over its length.

15. The stent of claim 13 including at the distal end a fusible link in the core body, the core body being conductive so as to soften the link when desired.

* * * * *